US00PP27328P3

(12) United States Plant Patent
Kapustra

(10) Patent No.: US PP27,328 P3
(45) Date of Patent: Nov. 1, 2016

(54) ***ABELIA* PLANT NAMED 'ABENOV41'**

(50) Latin Name: ***Abelia* hybrid**
Varietal Denomination: ABENOV41

(71) Applicant: Véronique Kapustra, Paris (FR)

(72) Inventor: Véronique Kapustra, Paris (FR)

(73) Assignees: INSTITUT NATIONAL DE LA RECHERCHE AGRONOMIQUE (INRA), Paris (FR), part interest; SAPHINOV S.N.C., Beaufort en Vallee (FR), part interest ( * ) Notice: Subject to any disclaimer, the term of this patent is extended or adjusted under 35 U.S.C. 154(b) by 0 days.

(21) Appl. No.: 14/545,920

(22) Filed: Jul. 8, 2015

(65) Prior Publication Data

US 2016/0100514 P1 Apr. 7, 2016

(30) Foreign Application Priority Data

Oct. 6, 2014 (EM) ..... 20142384

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Penny J. Aguirre

(57) ABSTRACT

A new cultivar of *Abelia* plant named, 'ABENOV41' that is characterized by its an evergreen plant habit in U.S.D.A. Zone 7, its long and floriferous bloom period, blooming from May to October in France, its large flowers that are pink-violet in color and open from deep pink-purple buds, its bracts that are reddish brown in color, and its moderate to vigorous growth habit.

2 Drawing Sheets

Botanical classification: *Abelia* hybrid.
Varietal denomination: 'ABENOV41'.

BACKGROUND OF THE INVENTION

The present invention relates to a new and distinct cultivar of *Abelia* of hybrid origin and will be referred to hereafter by its cultivar name, 'ABENOV41'. 'ABENOV41' represents a new *Abelia,* a shrub grown for landscape use.

The new cultivar is the result of a controlled breeding program conducted by the Inventor in Angers-Beaucouzé, France. The objective of the breeding program is to develop new cultivars of *Abelia* twith increased cold hardiness and unique flower colors and plant habits.

The new cultivar arose from a cross made by the Inventor in June of 2004 between *Abelia schumannii* 'Bumblebee' (not patented) as the female parent and *Abelia×grandiflora* 'Semperflorus' (not patented) as the male parent. The Inventor selected 'ABENOV41' as a single unique plant amongst the seedlings that resulted from the above cross in 2006.

Asexual propagation of the new cultivar was first accomplished by softwood stem cuttings by the Inventor in Angers-Beaucouzé, France in September of 2006. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'ABENOV41' as a unique cultivar of *Abelia.*

1. 'ABENOV41' exhibits an evergreen plant habit in U.S.D.A. Zone 7.
2. 'ABENOV41' exhibits a long and floriferous bloom period; blooming from May to October in France.
3. 'ABENOV41' exhibits large flowers that are pink-violet in color and open from deep pink-purple buds.
4. 'ABENOV41' exhibits bracts that are reddish brown in color.
5. 'ABENOV41' exhibits a moderate to vigorous growth habit.

'Bumblebee', the female parent plant of 'ABENOV41', differs from 'ABENOV41' in having a more compact plant habit, in being less floriferous, and in having smaller flowers that are pale mauve in color. 'Semperflorus', the male parent plant of 'ABENOV41', differs from 'ABENOV41' in having smaller flowers that are white in color, in having foliage that is bright green in color, and in having a shorter blooming period (July to August in France). 'ABENOV41' can also be compared to the *Abelia* cultivars 'Edward Goucher' (not patented) and typical plants of the species *Abelia engleriana* (no patented cultivars known to the Inventor). 'Edward Goucher' is similar to 'ABENOV41' in overall plant shape and flower color. 'Edward Goucher' differs from 'ABENOV41' in having flowers that are smaller in size, in having foliage that is brighter green in color, and in being less floriferous. Typical plants of the species *Abelia engleriana* are similar to 'ABENOV41' in having a moderate to vigorous growth habit and in flower color. Typical plants of *Abelia engleriana* differ from 'ABENOV41' in having deciduous plant habits and in having a shorter blooming periods.

BRIEF DESCRIPTION OF THE DRAWINGS

The accompanying colored photographs illustrate the overall appearance and distinct characteristics of the new *Abelia.*

The photograph in FIG. 1 was taken of a 3 year-old plant in the garden and provides a side view of the plant habit 'ABENOV41' in the early summer.

Figure 1:
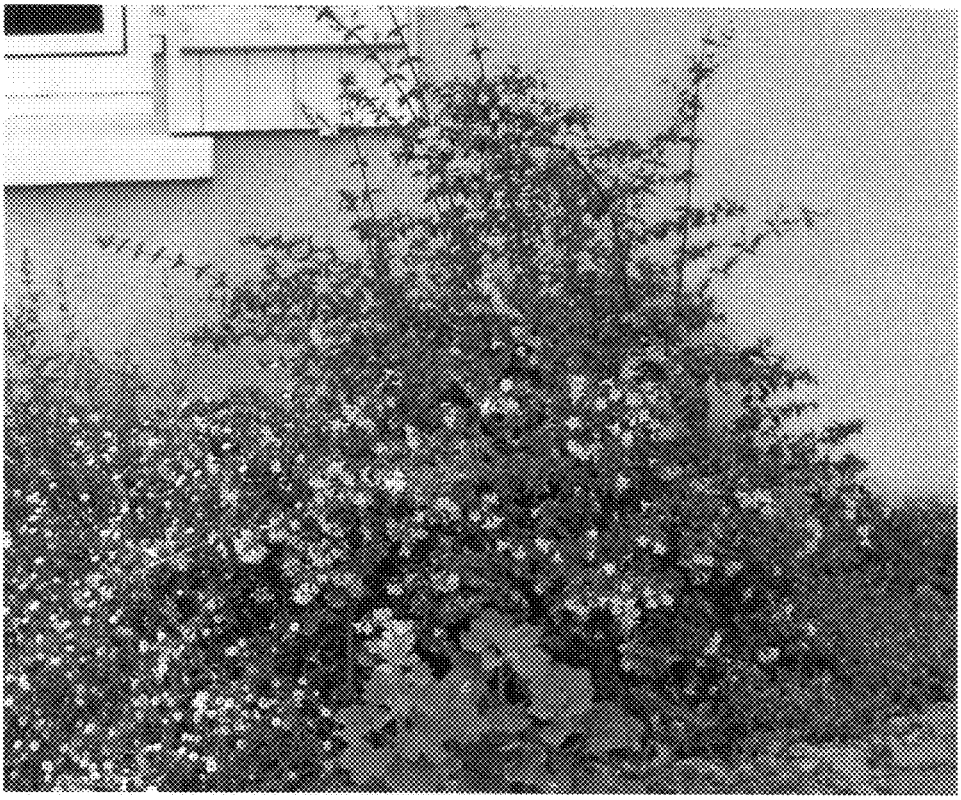
Figure 2:
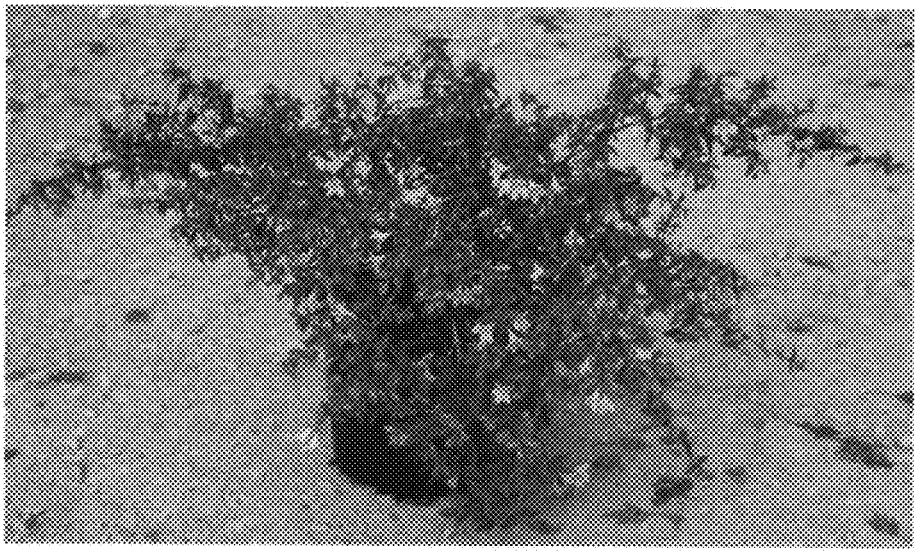

The photograph in FIG. 2 was taken of a plant 4 years in age as grown in a 17-liter containier provides a side view of a plant of 'ABENOV41' in the fall.

Figure 3:
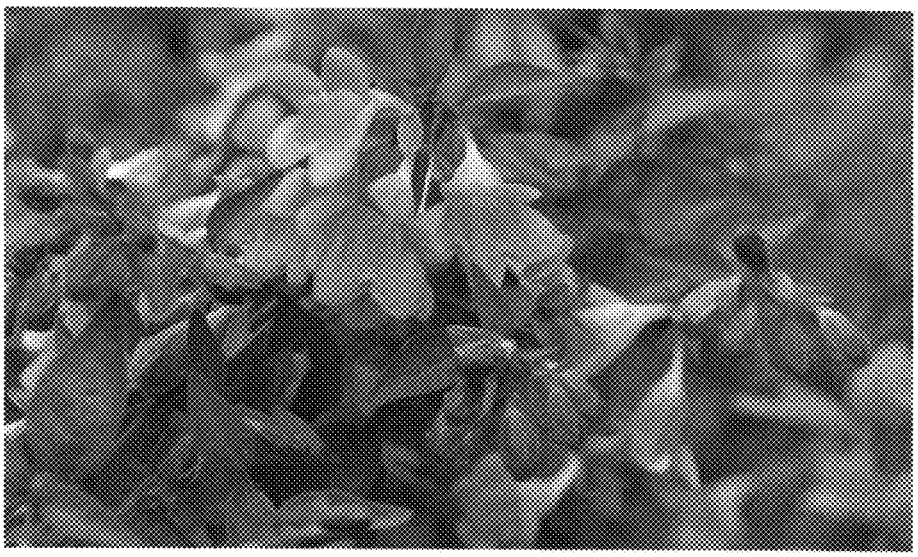

The photograph in FIG. 3 was taken of a 3 year-old plant in the garden and provides a close-up of the flowers and flower buds of 'ABENOV41' in mid summer.

The colors in the photographs are as close as possible with the photographic and printing technology utilized and the color values cited in the Detailed Botanical Description accurately describe the colors of the new *Abelia*.

DETAILED BOTANICAL DESCRIPTION

The following is a detailed description of one year-old plants of the new cultivar as grown outdoors spring through fall and in a greenhouse in 15-cm containers in winter in St. Paul, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—May to October in France.

*Plant type.*—Evergreen shrub (depending on frost level).

*Plant habit.*—Spreading and broadly upright.

*Height and spread.*—An average of 1.75 m in height and 1.35 m in spread.

*Cold hardiness.*—At least to U.S.D.A. Zone 7.

*Diseases and pests.*—No susceptibility or resistance to pests and diseases has been observed.

*Root description.*—Very fine and fibrous, 161D in color.

*Propagation.*—Softwood stem cuttings.

*Time required for root development.*—Roots initiate in about 60 days at 20° C. and fully develop in about 18 months in a P9 container in France.

*Growth rate.*—Moderate to vigorous.

Stem description (main branches and lateral branches):

*Stem color.*—Young and mature stems; 146D and suffused with 176B, mature wood: a blend of 199d and 156C.

*Stem size.*—Main stems; up to 64 cm in length and an average of 4 mm in diameter (in center region), lateral branches; an average of 11 cm in length and 2 mm in diameter.

*Stem quantity.*—Average of 5 basal branches and 16 lateral branches per basal branch.

*Stem shape.*—Rounded.

*Stem surface.*—Dull and sparsely pubescent on basal and lateral branches, mature wood is finely barked.

*Stem aspect.*—Very strong, held horizontal to upward with lateral stems held at about a 45° angle to main stems.

*Internode.*—Average of 3 cm in length.

*Branching habit.*—Free branching.

Foliage description:

*Leaf division.*—Single.

*Leaf attachment.*—Petiolate.

*Leaf arrangement.*—Opposite.

*Leaf number.*—Average of 12 (6 pairs) on basal stem 40 cm in length, an average 12 (6 pair) on a lateral stem 12 cm in length.

*Leaf shape.*—Ovate.

*Leaf apex.*—Acuminate.

*Leaf surface.*—Upper surface satiny to glossy and lower surface dull to satiny (when mature).

*Leaf base.*—Rounded to broadly cuneate.

*Leaf venation.*—Pinnate, color matches leaf coloration, veins on lower surface are pubescent.

*Leaf margin.*—Entire to very slightly sinuate.

*Leaf color.*—Immature upper and lower surface; 144A, mature upper surface; N137 to N137B, mature lower surface; a color between 137D and 138A.

*Leaf size.*—Average of 3 cm in length and 2.2 cm in width, up to 5.2 cm and 3.8 cm when mature.

*Petioles.*—Average of 1.5 mm in diameter and 3 mm in length, both surfaces a color between 137D and 138A, surface texture is moderately pubescent.

Flower description:

*Inflorescence type.*—Single flowers arranged at terminal nodes of secondary branches.

*Inflorescence size.*—Average of 5 cm in height and width (with one flower open and one mature bud, blooming area as flowers are single at upper leaf nodes).

*Flower fragrance.*—Faint, sweet.

*Flower quantity.*—Average of 4 per inflorescence.

*Flower lastingness.*—Average of 5 days.

*Flower buds.*—Obovate in shape, slightly curved downward, average of 7 mm in diameter and 1.5 cm in length, N77B in color, pubescent surface texture.

*Flower aspect.*—Outward to slightly pendent.

*Flower shape.*—Campanulate.

*Flower size.*—An average of 2.5 cm in depth and 2.5 cm in diameter.

*Petals.*—Average of 5, lower ⅔ fused, tube portion 1.8 cm in length and width, free lobes; margin is entire, apex is obtuse to broadly cuneate, ovate in shape, average of 8 mm in length and width, outer surfaces texture (tube and lobes) glabrous, inner surface is smooth and covered with soft hairs and are 1 mm in length and NN155B in color, color: inner and outer surfaces when opening and mature; NN155A and heavily suffused with N77B (effectively pink-violet) and base NN155A.

*Calyx.*—Persistent, ornamental, comprised of 2 sepals arranged opposite to each other.

*Sepals.*—2, broadly elliptic in shape, margin is entire, apex is obtuse (slightly acute), base is cuneate, upper and lower surfaces textures are smooth and dull, color: immature upper and lower surface; 162B and heavily suffused with 175A, mature upper and lower surfaces; 146B and suffused with 175A, about 6 mm in width and 75 mm in length.

*Peduncles.*—Average of 5 mm in length and 1 mm in width, strong, 144A in color and heavily suffused with 183B, surface texture is ridged vertically and pubescent with hairs about 0.75 mm in length and 155A in color.

*Pedicels.*—None, flowers are single.

Reproductive organs:

*Gynoecium.*—1 pistil, about 2.2 cm in length, stigma is club-shaped, 158A in color, and about 1.5 mm in diameter, style is about 2 cm in length and <1 mm in width, NN155A in color, ovary is globose in shape, about 1.5 m in diameter, and 145D in color.

*Androcoecium.*—4 stamens, anthers are oblong in shape, basifixed and hang downward, about 2 mm in length and 162A in color, filaments are about 1.3 cm in length and 157B in color, pollen is moderate in quantity and 161B in color.

*Fruit and seed.*—No fruit or seed have been observed.

It is claimed:

1. A new and distinct cultivar of *Abelia* plant named 'ABENOV41' as herein illustrated and described.

* * * * *